US011950943B2

(12) United States Patent
Pinault et al.

(10) Patent No.: US 11,950,943 B2
(45) Date of Patent: Apr. 9, 2024

(54) PATIENT SUPPORT DEVICE AND PATIENT POSITIONING SYSTEM

(71) Applicant: BIZLINK INDUSTRY GERMANY GMBH, Roth (DE)

(72) Inventors: Samuel Pinault, Chevreuse (FR); Claude Burlot, Bullion (FR)

(73) Assignee: BIZLINK INDUSTRY GERMANY GMBH, Roth (DE)

( * ) Notice: Subject to any disclaimer, the term of this patent is extended or adjusted under 35 U.S.C. 154(b) by 1000 days.

(21) Appl. No.: 16/323,684

(22) PCT Filed: Jul. 6, 2017

(86) PCT No.: PCT/EP2017/066938
§ 371 (c)(1),
(2) Date: Feb. 6, 2019

(87) PCT Pub. No.: WO2018/028901
PCT Pub. Date: Feb. 15, 2018

(65) Prior Publication Data
US 2019/0167212 A1    Jun. 6, 2019

(30) Foreign Application Priority Data

Aug. 12, 2016   (DE) .......................... 102016009853.8

(51) Int. Cl.
*A61B 6/04*     (2006.01)
*A61N 5/10*     (2006.01)
*B25J 9/16*     (2006.01)

(52) U.S. Cl.
CPC .......... *A61B 6/0487* (2020.08); *A61B 6/0407* (2013.01); *A61B 6/0464* (2013.01);
(Continued)

(58) Field of Classification Search
CPC ... A61B 6/0487; A61B 6/0407; A61B 6/0464; A61N 5/1049; A61N 2005/1057; A61N 2005/1074; A61G 7/1042; B25J 9/1694
See application file for complete search history.

(56) References Cited

U.S. PATENT DOCUMENTS 3,627,250 A * 12/1971 Pegrum .................... A61N 5/01
378/65
3,751,028 A *  8/1973 Scheininger ............. A61B 6/04
5/601
(Continued)

FOREIGN PATENT DOCUMENTS

DE          3201021        7/1983
DE          3336857        4/1985
(Continued)

OTHER PUBLICATIONS

EP-2883500-A1 English Translation (Year: 2015).*
DE 4021102 A1 English Translation (Year: 1990).*
EP-2883567-A1 English Translation (Year: 2013).*

*Primary Examiner* — Justin C Mikowski
*Assistant Examiner* — Amanda L Bailey
(74) *Attorney, Agent, or Firm* — TAROLLI, SUNDHEIM, COVELL & TUMMINO L.L.P.

(57) ABSTRACT

The disclosure relates to a patient support device (10) that is connectable to a positioning system (12), such as a multi-joint robot (16), the patient support device (10) comprising: a patient support region (18), comprising a front area (22) which defines a support plane (S) for supporting and/or contacting a patient (P) and an underside area (23) substantially facing away from the front area (22); and a coupling region (26) that is configured to be coupled to the positioning system (12), wherein the support plane (S) at least partially extends between the coupling region (26) and the underside area (23). The disclosure further relates to a
(Continued)

patient positioning arrangement comprising such a patient support device (10) and positioning system (12).

20 Claims, 9 Drawing Sheets

(52) U.S. Cl.
CPC .......... *A61N 5/1049* (2013.01); *B25J 9/1694* (2013.01); *A61N 2005/1057* (2013.01); *A61N 2005/1074* (2013.01)

(56) References Cited

U.S. PATENT DOCUMENTS

| | | | | |
|---|---|---|---|---|
| 4,842,259 | A * | 6/1989 | Rice | A61B 6/0464 5/601 |
| 4,894,855 | A * | 1/1990 | Kresse | B25J 9/0084 378/189 |
| 5,201,088 | A * | 4/1993 | Larsson | A61B 6/0407 5/601 |
| 7,552,490 | B2 | 6/2009 | Saracen et al. | |
| 7,860,550 | B2 | 12/2010 | Saracen et al. | |
| 7,938,578 | B2 | 5/2011 | Beimler et al. | |
| 8,126,114 | B2 | 2/2012 | Naylor et al. | |
| 8,734,014 | B2 * | 5/2014 | Scarpellini | A61B 6/0487 378/197 |
| 10,154,822 | B2 | 12/2018 | Henderson et al. | |
| 10,368,949 | B2 * | 8/2019 | Giulianotti | A61F 5/37 |
| 2005/0228255 | A1 * | 10/2005 | Saracen | A61B 6/548 600/407 |
| 2007/0169265 | A1 * | 7/2007 | Saracen | A61B 6/0487 5/601 |
| 2007/0189461 | A1 | 8/2007 | Sommer | |
| 2010/0069920 | A1 * | 3/2010 | Naylor | A61B 34/71 606/130 |
| 2011/0107515 | A1 * | 5/2011 | Brunker | A61N 5/10 5/601 |
| 2014/0046212 | A1 | 2/2014 | Deutschmann | |
| 2015/0327818 | A1 * | 11/2015 | Buck | A61G 13/04 5/608 |
| 2016/0073978 | A1 * | 3/2016 | Henderson | B25J 9/1676 901/11 |

FOREIGN PATENT DOCUMENTS

| | | | |
|---|---|---|---|
| DE | 3638953 | 5/1988 | |
| DE | 4021102 A1 * | 7/1990 | ............ A61B 6/02 |
| DE | 102006020868 | 10/2007 | |
| DE | 102007060690 | 6/2009 | |
| EP | 2687159 | 1/2014 | |
| EP | 2883500 | 6/2015 | |
| EP | 2883500 A1 * | 6/2015 | ........... A61B 6/0457 |
| EP | 2883567 A1 * | 6/2015 | ........... A61B 6/0457 |
| GB | 1312377 | 4/1973 | |
| JP | H7185024 | 10/1996 | |
| JP | H04307037 A | 10/2001 | |
| WO | 2005099578 A2 | 10/2005 | |

* cited by examiner

PATENT SUPPORT DEVICE AND PATIENT POSITIONING SYSTEM

CROSS REFERENCES TO RELATED APPLICATIONS

This application filed under 35 U.S.C § 371 is a national phase application of International Application Serial Number PCT/US2016/066938 filed Jul. 6, 2017, which claims priority to German Patent Application No. DE 10 2016 009 853.8, filed on Aug. 12, 2016, the disclosure of which is entirely incorporated herein by reference.

The disclosure relates a patient support device as well as a patient positioning system comprising a respective patient support device.

In the field of medical imaging as well as medical radiotherapy numerous solutions have been proposed for positioning a patient relative to an imaging and radiotherapy device by way of patient positioning systems. These often comprise kinematic structures, such as a multi-joint robot or robot arm. Moreover, patient support devices, such as a patient bed or couchtop, are known which are connected to such patient positioning systems for supporting and/or contacting a patient during the positioning.

The patient positioning system as well as patient support device need to fulfil a wide range of requirements. These relate, for example, to providing a flexible movability, a limited risk of interference with the surrounding, a limited interference with imaging or radiotherapy radiation, being arrangeable close to the floor surface (i.e., being able to assume a low loading position), having a limited weight and costs, and many more.

It has been found that known solution do not fulfil at least some of these requirements in a satisfying manner.

Accordingly, there is a need for a patient support device and patient positioning system being which is marked by an improved operability at limited costs.

According to the present disclosure, a patient support device is provided that is connectable to a positioning system, such as a multi-joint robot. The patient support device may generally be configured to support and withstand the static and/or dynamic loads exerted by a patient when being accommodated in the patient support device. This may include the patient's weight or acceleration forces when being moved by the positioning system in a treatment room (e.g. of a hospital). Note that in the context of the present disclosure, the patient may generally assumed to be an average adult person, e.g. with a size between ca. 1.50 m and 2 m and a weight between ca. 50 kg and 250 kg.

The multi-joint robot may be configured according to known solutions, for example, by comprising a plurality of links being connected by rotational or axial joints, thus defining an open kinematic chain between a typically stationary base region an end effector connecting portion of the robot. Alternatively or additionally, the positioning system may comprise a linear axis, which may also be connected to the above discussed multi-joint robot for translating it in space. Also, the positioning system may be floor-, wall- or ceiling-mounted. As detailed below, the present disclosure in particular contemplates a ceiling mounted solution. Note that the mounting to a respective floor, wall or ceiling area of a treatment room may involve directly connecting the positioning system to a respective area or, at least, to an intermediate member connected to or at least partially extending in parallel to e.g. said ceiling area.

The patient support device comprises a patient support region, comprising a front area which defines a support plane for supporting and/or contacting a patient and an underside area substantially facing away from the front area. The patient support region may be sized and/or shaped to accommodate a patient, in particular in such a manner that the patient can be stably positioned in space. For example, the patient support region may be configured to stably support a patient in a substantially upright sitting position and/or a substantially horizontal laying position. Note that supporting the patient may be achieved by a direct contact between the support region and the patient or by an at least in intermediate contact, e.g. when arranging and additional patient carrier structure in between the patient and support region.

The front area and underside area can, but need not be, planar. In general, they can have any curved, regular or irregular shape. The support plane may generally define a plane in which (or along which) a patient can be supported by the patient support device. As detailed below, this may include a seating and/or laying area for the patient as defined by the patient support region. Note that the support plane can, but need not be, limited to the front area of the patient support region. To put it differently, the support plane may generally be understood as an infinite virtual plane, whose position in space is defined by the patient support region of the patient support device.

The underside area may further be configured to face a floor area, at least when the patient support device is arranged so as to stably support a patient or, for example, so that the support plane extends substantially horizontally in space. Also, the underside area may generally be arranged in a region opposite to and facing away from the front area (e.g., at an underside of the patient support region whereas the front area is arranged at an upper side thereof).

The patient support device further comprises a coupling region that is configured to be coupled to the positioning system. The coupling may in particular include a mechanical coupling to the positioning system and may generally be permanent or releasable. Also, the coupling may involve forming electric and/or fluidic connections between the support device and the positioning system. In general, the coupling region may comprise an interface, such as a dedicated mechanical structure, for (in particular mechanically) connecting with a complementary structure of the positioning system. This may include generally known solutions, such as tool- or end-effector-connecting structures which are used in industrial robots (e.g. an electropneumatic tool-changer). In other words, the coupling region may comprise suitable engagement structures, such as undercuts, recesses or the like, so that the positioning system can engage therewith. The coupling region may further be substantially oval, circular or the like and/or may define a specific area for coupling to the robot.

The support plane at least partially extends between the coupling region and the underside area. In other words, the support plane may be enclosed or sandwiched by the coupling region and underside area, yet without necessarily contacting or intersecting the coupling region (such an intersection merely represents an option). In general, the patient support region may thus extend at least partially between the coupling region and underside area, for example, such that a patient may be at least partially be positioned between the coupling region and underside area.

In general, the coupling region may be spaced apart from the support plane and, when e.g. viewed along an axis extending orthogonally to and pointing away from the support plane (in particular without said axis intersecting the underside area), the coupling region may be positioned above the support plane. Likewise, the coupling region may be positioned opposite to the front area and/or support plane. Also, the coupling region may be remotely arranged from the underside area and, in particular, face away therefrom.

Generally, the coupling region may thus allow for arranging the patient support device at a positioning system such that the positioning system connects to the patient support device from above or, in other words, to an upper side thereof. Hence, the patient support device may be arranged at the positioning system in a hanging configuration. Also, the relative arrangement of support plane, coupling region and underside area may be chosen so that (at least when stably supporting a patient and/or the support plane being arranged substantially horizontally in space) the coupling region is arranged closer to a ceiling area of a treatment room than the support plane. Similarly, the support plane may be arranged between the coupling region and a floor area of the treatment room and generally be arranged closer to the floor area than said coupling region.

This arrangement of the coupling region is different from known concepts in which a positioning system supports a patient support device from below, e.g. by connecting a robot arm to a coupling portion provided at an underside area of a patient support region. As detailed below, this can provide numerous advantages, such as allowing the patient support device to be arranged very closely to an adjacent floor surface (e.g. since no interference of a robot arm connected to an underside area thereof with the floor area is possible). Also, this allows for a space-efficient installation of a positioning system and patient support device in a treatment room without occupying valuable floor space, in particular when using a ceiling-mounted positioning system.

The coupling region may further be positioned so that the patient support device is substantially self-balancing when being arranged at the positioning system. In other words, the coupling region may be positioned so as to allow for an arrangement at (and connection to) a positioning system, such that at least the static moments exerted by the patient support device on said positioning system are limited and, in particular, may substantially balance or neutralise each other. To put it differently, the coupling region may generally be positioned so as to allow for a coupling to the positioning system close to or substantially in line with a centre of gravity of the patient support device, especially when arranging the patient support device so as to stably support a patient (for example, with the support plane being substantially horizontal in space). The position of the coupling portion may also be selected in view of the arrangement of further monitoring systems, detection systems, movement instruction devices, display devices or the like at the patient support device which each affect its centre of gravity. Additionally or alternatively, the coupling region may be positioned in view of an expected average patient position and/or load exerted on the patient support device.

The patient support region may comprise at least one of a seating area (or sitting surface) and a laying area (or laying surface). These areas may form at least part of the front area, and may thus also at least partially define the support plane. The seating area and laying area may further be configured to support a patient (preferably an average adult patient as previously discussed) in a sitting and laying position, respectively. Specifically, the seating area and laying area may be configured so that a patient can be stably supported in an upright sitting or horizontal laying position, for example, for medical imaging or medical radiotherapy treatments.

According to a further embodiment, the patient support region comprises at least one of a patient seat and a patient couchtop. The patient seat may define a seating area as previously discussed and the patient couchtop may define a laying area as previously discussed. Also, they may at least from part of the front area, and may thus also at least partially define the support plane. As such, the patient seat may be limited to a certain region or area which is configured so that a patient may sit thereon. Furthermore, the patient couchtop may comprise a table- or patient-bed-structure on which a patient can lay down. Note that the patient seat may further comprise a backrest area, which, however, may be considered separately from the support plane of the patient support region. In the other words, the support plane may generally be considered as a plane by or in which the patient can be fully and sufficiently supported for assuming a predetermined position (such as a laying or sitting position). This may be achieved by a seat area or couchtop but not merely by a backrest area of a patient seat which, for example, may not achieve to sufficiently support and secure the vertical position of the patient in space.

Note that the seating area and/or the patient seat may generally be limited in size so that a patient can merely sit thereon but not horizontally lay down thereon in a stable and comfortable manner.

The coupling region may further be arranged in such a manner that it can be projected into the front area of the patient support region, and optionally, wherein said projection takes place along an axis extending substantially orthogonally to the support plane. In other words, the coupling region may generally be spaced apart from the front area and/or support plane of the patient support region and arranged oppositely to or above said front area/support plane. The projection may relate to a virtual projection without taking any intermediate structures or obstacles between the coupling region and the patient support region into account. Yet, the protection may exclude crossing or intersecting the underside area of the patient support region. To put it differently, the coupling region may be arranged in such a manner that it overlaps with the patient support region and, in particular, a front area thereof or a general region for contacting and/or supporting a patient.

According to a further aspect, the coupling region and patient support region are connected by a connecting region which, optionally, at least partially extends at an angle to the support plane.

As a general matter, the patient support device and in particular its patient support region, coupling region and/or connecting region may be comprised by a one-piece member or by a multi-piece assembly. Also, the respective regions may be formed by individual members (e.g. a patient support member forming the patient support region, a coupling member forming the coupling region and/or a connecting member forming the connecting region). Alternatively, the patient support device may comprise members which form at least part of numerous regions, such as a connecting member also comprising a section which contributes to the front area of the patient support region.

The connecting region may comprise a section extending at an angle and in particular substantially orthogonally to the support plane. This section may be referred to as a central section of the connecting region. Also, the connecting region may be directly connected to the patient support region or connected thereto by further intermediate sections of the connecting region (e.g. intermediate angled sections). Again, note that each of the sections or portions of the connecting region may be formed by an individual member or an assembly of numerous members.

Furthermore, the connecting region may comprise a section extending at an angle to the central section or, in general, at an angle between ca. 0° and 80° and in particular between ca. 0° and 30° to the support plane, or be extend substantially in parallel to the support plane. This section may be referred to as top section. Said top section may generally be arranged at an end portion of the central section being remote from and/or facing away from the patient support region. Also, the top section may be connected to or comprise the coupling region. In other words, the top section may extend substantially horizontally from the coupling region and connect to the, for example, substantially vertical central section of the connecting region which again connects to the substantially horizontal support plane, for example, by means of substantially horizontal lower section of the connecting region. Note that these spatial relations relate, in particular, to a scenario of arranging the patient support device so as to stably support a patient and/or of arranging the support plane substantially horizontally in space.

According to a further example, the patient support device or at least its connecting region is at least one of substantially C-, bow- and arc-shaped and/or defines a polygonal profile having at least one open side region. The respective shapes and/or profiles may be defined in a plane extending substantially orthogonally to the support plane, i.e., generally relate to a cross-sectional shape or profile. The open side region may be positioned such that a patient may easily access or exit the patient support device and in particular the support plane.

The connecting region may further comprise at least one area which is permeable for at least one of medical radiotherapy radiation and medical imaging radiation, said area optionally comprising a through-hole. The permeable area may be provided in a connecting region and/or the patient support region. In one embodiment, the patient support region comprises a patient seat and the connecting region comprises a central section extending at an angle to the patient support region (and preferably substantially orthogonally thereto). Said central section may further comprise a through-hole allowing for an accessibility of a back and/or neck region of a patient sitting upright on the patient seat by the above-mentioned radiation. Note that in this context, the central section may include a backrest-area for the patient, said through-hole extending through the backrest-area.

The patient support region may further comprise a displaceable member defining at least part of the front area (and in particular the support plane), the displaceable member being configured to be displaced in such a manner that a patient's position within the patient support device can be changed. For example, the displaceable member may be moved relative to an as such stationary or non-movable portion of the patient support device and/or the patient support region. The displacement may comprise a sliding or translational motion of the displaceable member. In one example, the displaceable member is configured to be displaceable in such a manner, that the patient's position within the support plane can be changed and/or that the displacement of said member may generally take place within or in parallel to the support plane. Also, the patient's position may be generally adjusted so as to move closer to at least one of a connecting region, coupling region, geometric centre and centre of gravity of the (in particular unloaded) patient support device.

The displaceable member may be connected to as such stationary parts of the patient support device by way of (in particular linear) guide structures, such as guide rails, roller tracks or the like. Said guide structures may be arranged in and/or along edge regions of the patient support region, wherein said edge regions may connect to the support plane. In one example, the patient support region comprises a patient couchtop and the guide structures are arranged along edge regions of the couchtop and comprise guide rails which receive rollers connected to the displaceable member. This may in particular relate to a substantially rectangular or oval couchtop and the guide structures extending along the longer sides and edge regions thereof.

The displaceable member may further provided as a planar or plate-type member forming at least part of a laying area of the patient support region. This way, after a patient sits or lays down on the displaceable member, said member may be displaced by means of the above discussed guide structures.

Accordingly, in a loading position (e.g. for providing easy access for the patient), the displaceable member may be displaced so as to form an elongated portion of the patient support device and/or patient support region. In a treatment position, on the other hand, the displaceable member may be arranged in an substantially non-displaced start position, with the patient support device and/or patient support region having a comparatively smaller length. Note that the respective length-measurements may relate to dimensions of the patient support device and/or patient support region within the support plane and in particular along longitudinal axes thereof.

The displaceable member may be configured to at least partially support a patient and, optionally, the displaceable member may comprise at least part of a seating and/or laying area of the patient support region. Accordingly, the displaceable member may form at least part of a patient couchtop on which a patient may fully or at least in part lay down to then being displaced, e.g. along the above discussed linear guide structures, within the support plane. This may be referred to as a trolley-like displacement.

The patient support device comprises at least one movement instruction device for receiving operator inputs for moving the patient support device by way of the positioning system. The movement instruction device may comprise known structures such as a joystick or a navigation key unit. It is also conceivable to provide an operating section connected to a force sensor, for moving the positioning system in a force-controlled manner. Yet, for reducing the costs, the present disclosures particularly contemplates providing manual input elements having switch functions and/or handles as discussed in the following. Also, the movement instruction devices may generally generate signals which, e.g. by way of the coupling region, may be transmitted to control devices of the positioning system in a generally known manner. Said signals may prompt the positioning system to carry out the desired movements.

According to one example, the movement instruction device comprises at least one manual input element which, when being activated by an operator, provides signals which prompt the positioning system to move, in particular with a preset speed and/or in a preset direction. Said manual input element may be configured as a switch, which only provides respective activation-, speed- and/or direction-signals if being manually activated (e.g. pushed). Accordingly, the manual input element may generally be configured as a so-called "dead man switch".

The movement instruction device and especially its one or more manual input elements may be provided in designated areas of the patient support device and, in particular, in a connecting region and especially a central section thereof. In one example, the manual input element is comprised by a handle in such a manner that the handle can be simultaneously grasped by an operator while activating the input element. Also, a respective plurality of manual input elements may be provided, wherein the elements may each be configured to command one specific designated movement. According to one variant, a manual input element according to one of the above examples is provided for commanding each of a vertical motion, a vertical pivot motion, a longitudinal motion and a lateral motion. As a general matter, the manual input elements may be individually labelled and/or marked (e.g. by way of different colors) for improving operator orientation.

Additionally or alternatively, a manual input element may be provided for commanding a designated emergency motion, such as a combined vertical and longitudinal motion for arranging the patient support device in a predefined safe position in a treatment room.

The patient support device may further comprise at least one patient monitoring system, in particular wherein said patient monitoring system is configured to acquire information for monitoring at least one of a position of the patient and movements of the patient. The patient monitoring system may be configured to optically monitor the patient, e.g. by way of cameras or camera sensors, such as a structured light camera. The position of the patient may relate to an absolute position within space and/or within or relative to the patient support device. Also, said position may relate to only a predetermined region or body part of the patient. In general, the patient monitoring system may be configured to detect such positions at least when the patient assumes a predetermined treatment position in the patient support region (e.g. by sitting upright or laying down on the support plane). The movement of the patient may likewise relate to movements of the patient when assuming the predetermined treatment position. These movements may include respiration movements, which can e.g. be detected from respective motions of a chest region.

The patient support device comprises at least one display device that is configured to display information to at least one of an operator of the patient support device and a patient being accommodated in the patient support device. Similar to above, such display devices can be directly integrated into the patient support device and, at least in case of a display device for an operator, into a connecting region and especially a central section thereof. Note that the display device for an operator may generally face away from the patient support region and e.g. display information necessary for correctly positioning the patient support device by way of the positioning system. A display device for the patient, on the other hand, may generally face the patient support region and e.g. display information such as an optimal breathing rhythm which the patient should follow.

The patient support device may further comprise at least one detection system for detecting at least one of a predetermined target in the surrounding and a deformation state of the patient support region under a patient's load. Specifically, the detection system may be configured to detect an active target (which e.g. actively emits a detectable signal) and/or a passive target (which does not actively emit detectable signals, but can be detected e.g. based on its shape, color, reflective characteristics or the like).

In this context, the target may be provided at a designated position in the surrounding so as to detect a relative position of the patient support device to said designated position. The designated position may, for example, include or be positioned in a predetermined relative manner to a radiation isocentre of a medical imaging and/or medical radiotherapy device. This way, the relative position of the patient support device to said radiation isocentre can be detected.

Likewise, for detecting a deformation state of the patient support region, a target may be provided at the patient support region and may further be configured to change its absolute position in space in response a deformation state of said patient support region. For example, the target may generally be positioned at or adjacent to a region of a seating or laying area deflecting under the patient's load (and e.g. at an underside area thereof). According to one example, the patient support region comprises a patient couchtop which bends under a patient's load, the target being positioned in a region of said couchtop which equally bends. Thus, based on a detected position of the target, a bending state of the couchtop can be inferred upon.

In general, the detection system may comprise an optical detection system which, for example, is arranged at or adjacent to the underside area of the patient support region. The optical detection system may comprise suitable sensors and/or cameras e.g. for optically detecting a target as previously discussed. In one example, the optical detection system detects both of a target in the surrounding and a deformation state of the patient support region, e.g. by way of a further target being positioned at the patient support region as discussed above. This may be achieved, in particular, by positioning the detection system at the underside of the patient support region.

The patient support device may further comprise at least one internal channel for accommodating connecting lines, said internal channel being in particular configured to at least partially shield the connecting lines from the environment. Accordingly, the internal channel may be configured to guide connecting lines through the patient support device. In particular, the connecting lines may be guided from the coupling region to further devices comprised by the patient support device, such as the patient monitoring systems, movement instruction devices, detection systems and the like. Also, the connecting lines may be guided from the coupling region to further connecting elements (such as plugs or sockets) provided at an external region of the patient support device, e.g. for connecting external devices thereto.

As previously indicated, the coupling region may be configured to further connect said connecting lines to complementary lines provided in a respective coupling region of the positioning system. This way, the connecting lines may for the most part of their length or substantially completely be shielded from the environment, at least in the region of the patient support device. Also, the connecting lines may further be internally or externally guided through the positioning system to surrounding devices and/or supply systems. In general, the connecting lines may be configured to transmit electronic or data signals as well as power or fluids. In other words, the connecting lines may be provided in form of power and/or data cables as well as pipes, channels, hoses or the like.

The disclosure further relates to a patient positioning arrangement, comprising a patient support device according to any of previous aspects and a patient positioning system connected to the patient support device. As discussed above, the patient positioning system may comprise a multi-joint robot, e.g. comprising at least five rotational links for positioning the patient support device in space. Additionally or alternatively, the patient positioning system may comprise a linear axis, said linear axis being configured to translate the patient support device, and/or a multi-joint robot being arranged in between, in space. Furthermore, the positioning system may be ceiling mounted, and may thus generally be configured to connect to the coupling region of the patient support device from above.

The present disclosure will be further described based on the accompanying drawings, wherein.

In the following, specific details will be discussed, without being limited thereto, for promoting a complete understanding of the present disclosure. Yet, it is evident to the skilled person that the present disclosure can be used in connection with different embodiments which deviate from the details discussed below. Furthermore, numerous embodiments will be discussed, wherein similar or corresponding features will be marked by similar reference signs.

Figure 1:
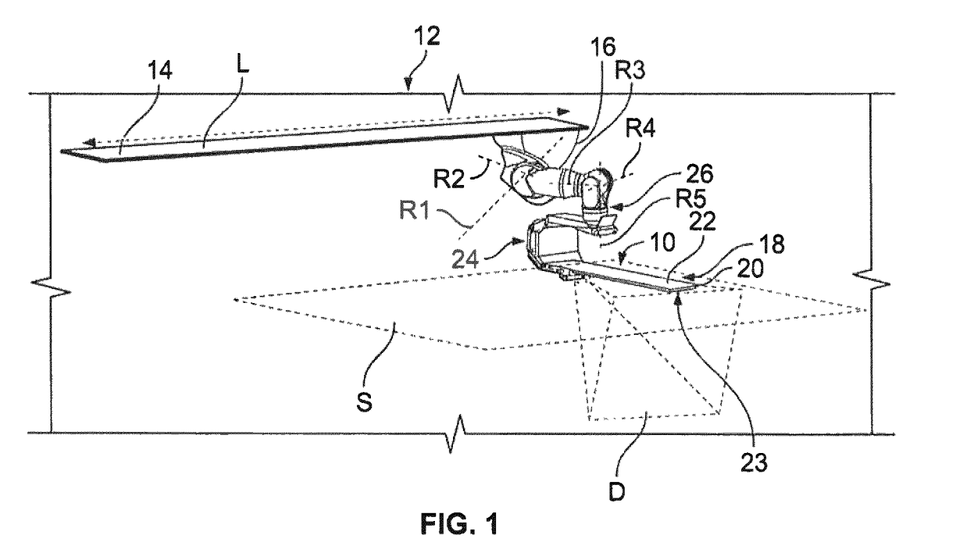
FIG. 1 shows a perspective view of a patient positioning system comprising a patient support device according to a first embodiment.

In FIG. 1, a patient support device 10 is shown which is arranged at and connected to a positioning system 12. The positioning system 12 comprises a linear axis 14 which is configured in a generally known manner. The positioning system 12 further comprises a mufti-joint robot 16, comprising five rotational joints each defining a respective rotational axes R1-R5. Said axes R1-R5 can, in a generally known manner, position the patient support device 10 within a treatment room accommodating the positioning system 12. Note that the rotational joints defining the axes R3-R5 may generally be referred to as a wrist section of the robot 16. The positioning system 12 and patient support device 10 together form a patient positioning arrangement.

As indicated by an arrow L in FIG. 1, the robot 16 is connected to the linear axis 14 in such a manner, so as to be translatable in space along said axis 14. Specifically, the linear axis 14 is mounted to a non-depicted ceiling area of the treatment room, so that the robot 16 generally extends towards a floor area of the treatment room. Accordingly, the patient support device 10 is generally arranged between a ceiling area and floor area of the treatment room by being connected to the robot 16 in a substantially vertically downwards hanging configuration.

As will be discussed in further detail below, the patient support device 10 comprises a patient support region 18. In the present example, said support region 18 comprises a patient couchtop 20 defining a laying area, so that a patient P can lay down thereon and be supported in a substantially horizontally laying manner. Accordingly, the patient support region 18 and its patient couchtop 20 comprise a front area 22 defining a (virtual) support plane S. In the example of FIG. 1, the support plane S is depicted as an infinite virtual plane in space. Yet, it may also be limited to e.g. the front area 22 of the patient support region 18. In general, said support plane S defines a plane for contacting a patient and thus a plane in (or at least in parallel to) which the patient P is arranged when being accommodated in the patient support device 20 in a stably supported manner (i.e., when laying down on the couchtop 20 with the back resting against the front area 22).

On the other hand, the patient support region 18 and its patient couchtop 20 define an underside area 23 which, in the depicted state, faces a floor area of the treatment room. The underside area 23 is arranged in an opposite region of the patient support region 18 compared to the front area 22 and generally faces away from said front area 22. Accordingly, it does not form part of the support plane S or provides any possibility for directly contacting or accommodating a patient P.

The patient support device 10 further comprises a coupling region 26 that provides an as such known mechanical coupling interface to an end portion of the wrist section of the robot 16 (e.g., to a tool- or end-effector-connecting portion of the robot 16).

The coupling region 26 and the patient support region 18 are further connected by a connecting region 24 of the patient support device 10. As further evident from the following figures, the connecting region 24 is generally C- or bow-shaped with opposite sections or legs of said C- or bow-shape each connecting to one of the couchtop 20 and coupling region 26. Accordingly, the couchtop 20 defines an elongated lower segment or leg of said C- or bow-shape, at least when the patient support device 10 is arranged so that the support plane S assumes a substantially horizontal position in space (cf. position as e.g. illustrated in FIGS. 1-3).

Figure 2:
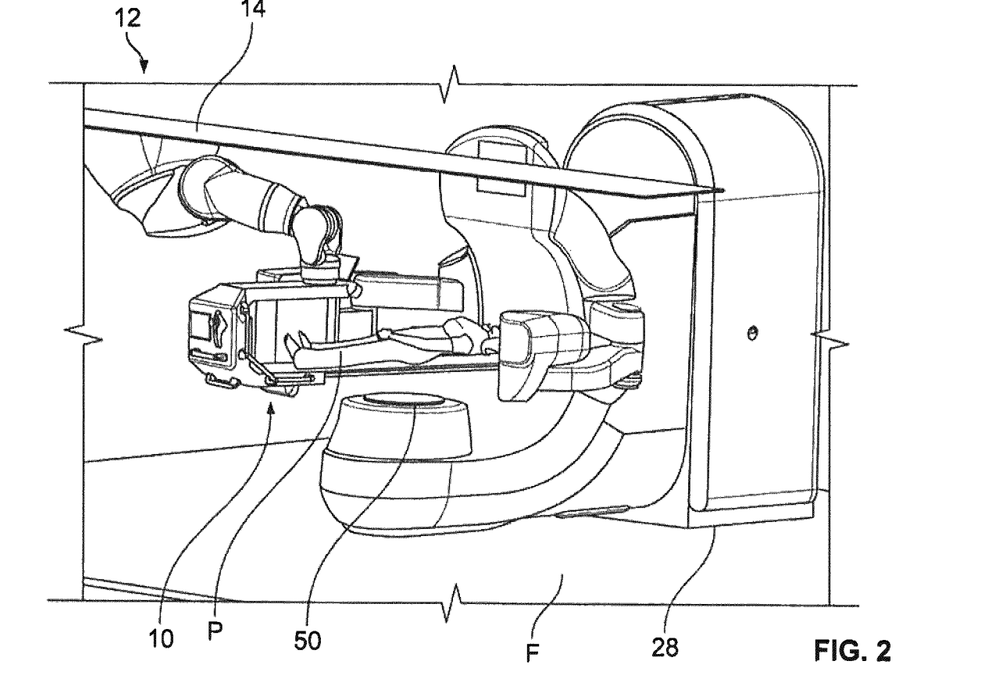
FIG. 2 shows a further perspective view of the embodiment according to FIG. 1, with the patient support device accommodating a patient and positioning said patient relative to a medical radiotherapy device.

The above configuration is further evident from the illustration in FIG. 2. In this figure, the positioning system 12 is depicted in a state of positioning the patient support device 10 accommodating a patient P in a working space of a medical radiotherapy device 28 (e.g. a standard LINAC-device). Again, one can see that the positioning system 12 comprises the linear axis 14 being arranged at a non-depicted ceiling area of the treatment room. On the other hand, FIG. 2 depicts the floor area F which extends substantially in parallel to said linear axis 14. Thus, it is further evident that in the state depicted in FIG. 2 in which the patient support device 10 is arranged to stably support the patient P, the couchtop 20 and thus also the front area 22 and support plane S defined thereby (cf. FIG. 1) are arranged substantially in parallel to the floor area F as well as substantially horizontally in space.

Figure 3:
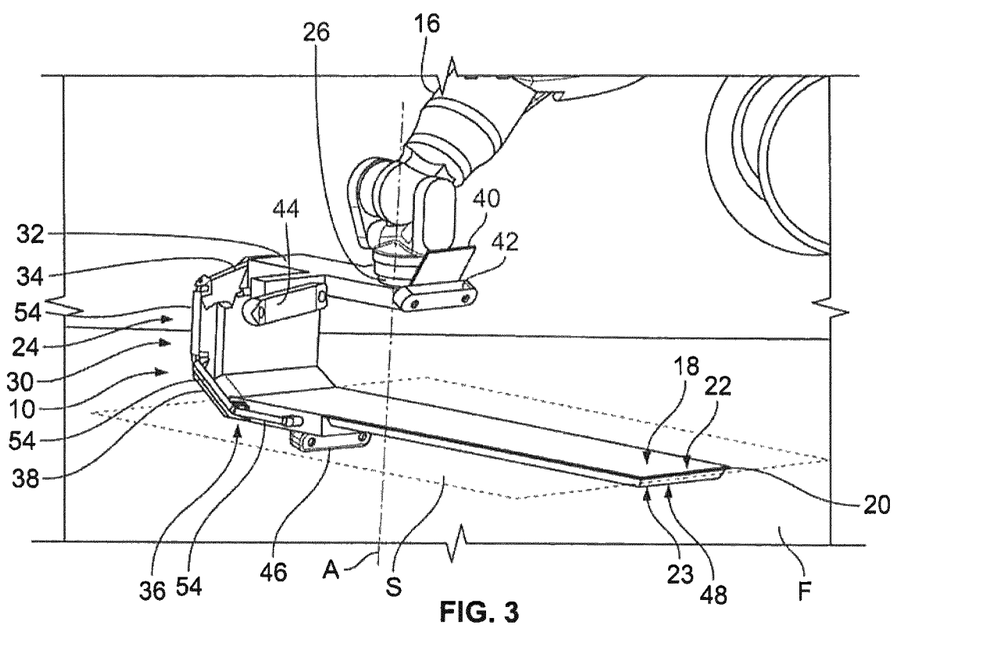
FIG. 3 shows a detailed perspective view of the patient support device according to the first embodiment.

FIG. 3 shows a detailed perspective view of the patient positioning system 10 as well as a wrist section of the robot 16 according to the previously discussed embodiment. Again, the coupling region 26 of the patient support device 10 is shown which is connected to the robot's wrist section.

Furthermore, the patient support region 18 comprising the couchtop 20 can again be seen whose front area 22 defines the support plane S (i.e., said support plane S being level with an upper surface or laying area of the couchtop 20). Still further, the underside area 23 of the patient support region is shown which faces away from the front area 22 and is spaced apart from the support plane S at least by the material thickness of the couchtop 20.

Accordingly, from FIG. 3, it is evident that the support plane S is arranged between the connecting region 26 and the underside area 23. This is in particular valid when viewed along an axis A extending orthogonally to the support plane S and (in the present example) intersecting the coupling region 26. Thus, contrary to known solutions, the robot 16 can connect to the patient support device 10 from above due to the arrangement of the support plane S between the underside 23 and coupling region 26.

Furthermore, FIG. 3 shows that the coupling region 26 can be projected into the front area 22 of the patient support region 18, for example, along the axis A. In other words, when viewed along said axis A, the coupling region 26 and front area 22 spatially overlap. Moreover, the coupling region 26 is positioned so that the axis A further intersects a centre of gravity of the patient support device 10. This way, the patient support device 10 is arranged in a self-balancing manner at the robot 16 so that, at least in a static state, no extensive moments are exerted onto the robot 16.

FIG. 3 also shows the configuration of the connecting region 24 in further detail. Specifically, said connecting region 24 comprises an upright central section 30 extending at an angle to the support plane S and, in the depicted case, extending substantially orthogonally thereto. The central section 30 is connected to the coupling region 26 by way of a top section 32. The top section 32 extends, for the most part, in parallel to the support plane S and front area 22 and merges into the central section 30 by way of an angled portion 34. Note that that merging between the central and top section 30, 32 takes place at a first end portion of the central section 30 facing away from the support plane S (i.e., facing a ceiling area in the state shown in FIG. 3).

Still further, the connecting region 24 comprises a lower section 36 which again extends largely in parallel to the support plane S and merges into the central section 30 by way of angled portion 38. Said merging takes place at a second end portion of the central section 30 opposite the first end portion and, in the state depicted in FIG. 3, facing the floor area F. Furthermore, from FIG. 3, it can be gathered that the lower section 36 extends along and partially overlaps underside area 23 of the patient support region 18. Note that in general, the connecting region 24 and patient support region 18 can be formed by one and the same member or an assembly of multiple members which, moreover, may also form part of both of the connecting and patient support region 24, 18.

Overall, from FIG. 3, it can again be seen that the patient support device 10 has an overall C- or bow-shape with the couchtop 20 forming an elongated lower side or leg thereof. This, in particular, relates to the connecting region 24 which due to the above discussed positions and orientations of the central, top and lower sections 30, 32, 34 defines an overall C-shape on its own. Furthermore, as a general aspect of the present disclosure, it becomes evident that the coupling region 26 is located above the front area 22 of the patient support region 18, so that the robot 16 can connect to the patient support device 10 from above, i.e. facing the front area 22 and not the underside area 23.

Note that the state according to FIG. 3 shows a position of the patient support device 10, so that it can stably support a patient P laying down on the couchtop 20, and wherein the support plane S and the patient P are arranged substantially horizontally in space. In the present example, this also means that in said state, the couchtop 20 and the support plane S both extend substantially in parallel to the floor area F and/or the ceiling area of the treatment room. Also, the robot 16 extends substantially downwards from said ceiling area, so that its wrist section generally connects to an upper side region of the patient support device 10, said upper side region being opposite to and facing away from the underside area 23. Accordingly, when stably supporting a patient, the support plane S will be arranged more closely to a floor area F of the treatment room than the coupling region 26 as well as the wrist section of the robot 16 which instead will be arranged closer to the ceiling area. Accordingly, the support plane S generally extends between the floor area F and the coupling region 26 as well as the wrist section of the robot 16 and ceiling area.

In the following, further devices and systems which are directly integrated and embedded into the patient positioning system 10 will be discussed with reference to FIGS. 3-5. An advantage of this integration is that the number of independent devices in the treatment room which need to be separately handled and arranged and each pose a risk of interfering with the robot 16 can be reduced. Furthermore, the patient support device 10 can be delivered to a customer as a highly integrated system providing numerous functionalities required for carrying out medical imaging and/or medical radiotherapy procedures, such that the setup, maintenance and installation process of a treatment room can be simplified.

First of all, in FIG. 3 a display device in form of a so-called gating screen 40 is shown. Said screen 40 displays in a generally known manner and optimal breathing/respiration rhythm to the patient P for improving the quality of the treatment. A first patient monitoring system comprising a camera 42 monitors the patient's respiratory movements. Note that both of the screen 40 and camera 42 are connected to the top section 32 of the connection region 24 and are located close to the coupling region 26 while facing the front area 22 of the patient support region 18.

Figure 6:
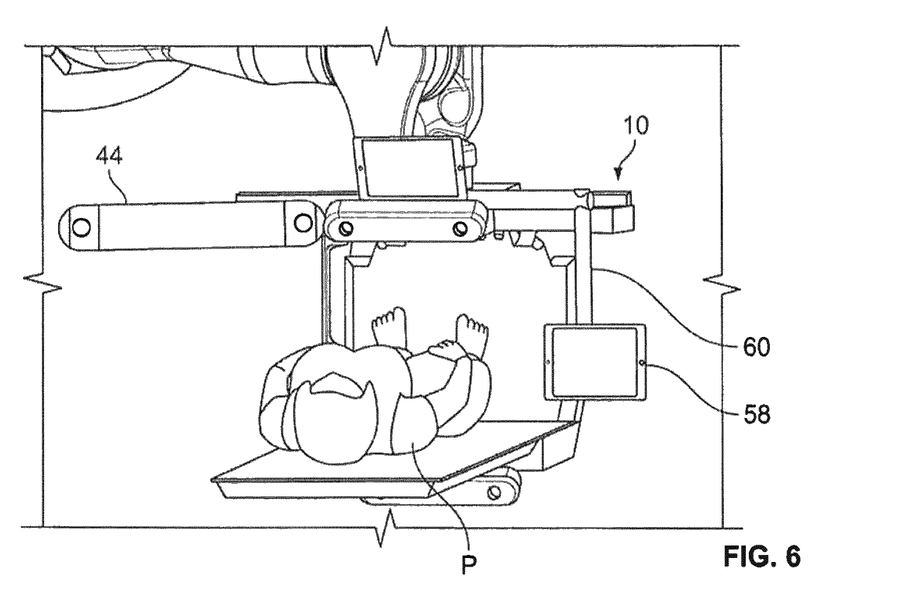
FIGS. 6, 7 show a perspective view of a patient support device according to a further embodiment.
Figure 7:
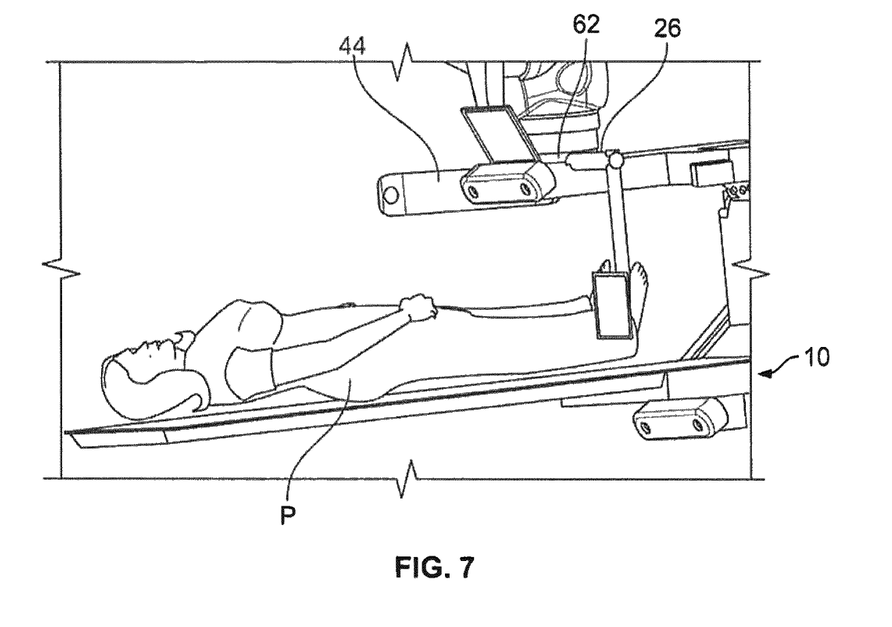

Furthermore, a further patient monitoring system in form of a structured light camera 42 is arranged at a side region of the connecting region 24 while again generally facing the front area 22 of the patient support region 18 (see also FIGS. 6, 7). This structured light camera 42 monitors, in a generally known manner, the position of the patient P within the patient support device 10, e.g. by acquiring image data based on which a 3D-model of the patient can be generated.

Still further, at the underside area 23, a detection system 46 in form of a further camera is provided. Said camera 46 generally faces a surrounding region of the patient support device 10 and, more specifically, generally faces the floor area F as well as a first end portion of the patient support region 18 facing away from the connecting region 24. As shown in FIG. 1 by dashed lines, the camera 46 thus defines a detection space D which intersects the floor area F as well as the underside area 23 of the couchtop 20. As indicated in FIG. 3, at the underside area 23 and in the region of the first end portion of the patient support region 18, passive targets 48 in form of stickers having a dedicated optically recognizable pattern, such as a barcode or the like, as well as a dedicated color and/or reflective characteristics are provided.

The camera 46 is configured to detect these targets 48, such that a position thereof can be determined (e.g. an absolute position in space or a position relative to the camera 46). Based on said determined position, a deformation state of the patient support region 18 and, specifically, of the couchtop 20 under a patient's load can be determined. More precisely, the couchtop 20 may generally be formed of a material which bends under a patient's load, such as carbon fibre. The amount of bending can hence be determined based on the image data acquired by the camera 46 and the thereby detected positions of the targets 48.

Note that a similar target 50 may be provided at a radiation isocentre of the LINAC-device 28 or in a predetermined relative positional relationship thereto. This target 50 forms a target in the surrounding of the patient support device 10 which can equally be detected by the camera 46. Again, based on the acquired image data, a position of said target 50 can be determined, e.g. for checking whether the patient support device 10 is arranged in a desired manner relative to said radiation isocentre.

As a general aspect of the present disclosure, the patient support device 10 may also comprise a processor or central processing unit CPU for processing the image data acquired by at least one of the cameras 42, 44, 46 (e.g. for directly determining the relevant positions of the patient P and/or targets 48 or the patient's respiratory movements). Additionally or alternatively, suitable connecting lines such as data cables may be provided for connecting these devices to a remote processor or computing device. These connecting lines may run through internal channels to the coupling region 26, to then be connected to further cables within the robot 16 and be guided along the ceiling area or linear axis 14 towards respective remote processor or computing devices.

Figure 4:
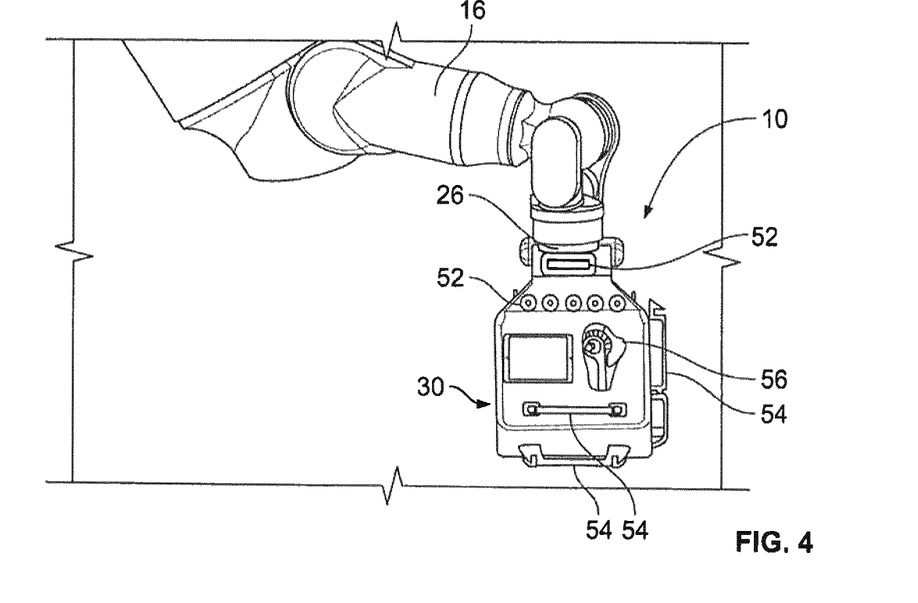
FIG. 4 shows a rear view of a connecting region of the patient support device according to a further embodiment.
Figure 5:
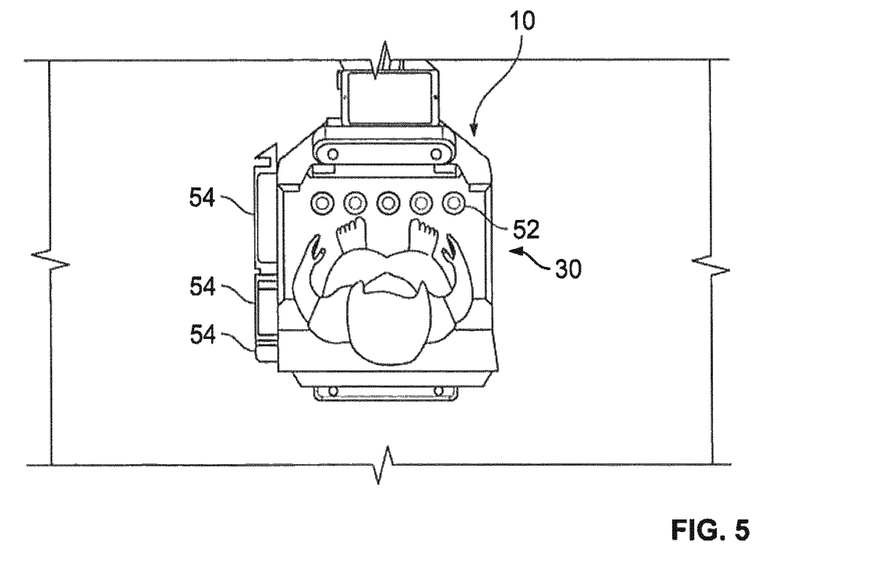
FIG. 5 shows a front view of the patient support device according to FIG. 4.

In FIGS. 4 and 5, a front and rear view of the patient positioning system 10 in a state similar to FIG. 2 is shown and, more specifically, a front and rear view of the central section 30. Note that in this case, the patient positioning system 10 is configured according to a further embodiment by not comprising the structured light camera 44. Instead, at a rear side of the central section 30 facing away from the patient P (and the patient support region 18, cf. FIG. 4) as well as a front side thereof facing towards the patient P (and the patient support region 18, cf. FIG. 5), connecting elements 52 in form of five circular connecting plugs and/or sockets for fluid lines, cables, electrodes or the like are provided. These can be used for connecting necessary devices to the patient support device 10 and/or the patient P, e.g. when performing a medical imaging or radiotherapy treatment under anesthesia. Note that such connecting elements 52 may likewise be incorporated in the embodiment according to FIG. 3.

Furthermore, from FIG. 4 it can be gathered that a further display device 52 is provided at the rear side of the central section 30. Said display device displays information to an operator of the patient support device 10 and positioning system 12.

Furthermore, numerous movement instruction devices 54 in form of coloured handles are provided. These handles 54 represent manual input elements which each comprise a switch function such that an operator can simultaneously grasp the handle 54 and, e.g. by way of exerting a slight pressure thereon, activate said switch function. Each handle 54 is associated with a predetermined movement direction of the patient support device 10 so that if activating the respective switch function, control signals will be generated and transmitted to a controller of the robot 16. Consequently, a movement of the patient support device 10 with a predetermined speed in said predetermined movement direction will take place. On the other hand, as soon as the handles 54 and its switching functions are released, the movement in the respective direction will stop ("dead-man switch"). Furthermore, at least one of the handles 54 may be associated with a predetermined emergency movement, e.g. for quickly arranging the patient support device 10 in a safe position within the treatment room. Note that similar to FIGS. 4 and 5, the embodiment according to FIG. 3 also includes numerous movement instruction handles 54.

Finally, an emergency-switch 56 is provided at the rear side of the central section 30. Also, a connector 52 for power and signals is provided close to the coupling region 26.

Note that any of the previously discussed integrated systems and devices as shown in FIGS. 3 to 5 can be connected to further devices, processors, power supplies, fluid reservoirs or the like by way of connecting lines (such as data or power cables or hoses, pipes etc.). In the depicted embodiments, however, these connecting lines are accommodated in internal channels within the patient support device 10. In other words, these connecting lines are not guided along an exterior surface portion of the patient support device 10, which may be done at most over a limited share of their overall lengths. Furthermore, as previously indicated, these connecting lines may extend to the coupling region 26 and thereby be coupled to complementary lines accommodated in internal channels within the robot 16. These complementary lines then extend towards further remote devices, power storages and/or fluid reservoirs within the treatment room.

A further example for integrating systems into the patient support device 10 is shown in the embodiment according to FIGS. 6 and 7. Said embodiment is based on the example of FIG. 3 and shows the position of the structured light camera 44 in further detail. In addition to said previous example, the embodiment of FIGS. 6 and 7 comprises an additional display device 58 in form of a further screen, which is connected to a holding structure 60. Said holding structure 60 generally defines an angle by connecting two circular profiles in an orthogonal manner. Furthermore, said holding section 60 connects to the coupling region 26 of the patient support device 10 by way of a ring element 62. Said ring element 62 comprises a rolling ring or bearing so that it can be rotated about the coupling region 26 about an axis similar to axis A of FIG. 3. This way, the screen 58 can be flexibly pivoted relative to the patient P.

Note that as a general aspect of the present disclosure, any of the previously discussed integrated devices and embedded systems may be combined with one another, including omissions or additions of further devices and systems compared to the specific examples shown in FIGS. 3 to 7. For example, the present disclosure also contemplates configuring a rear side of the central section 30 in FIG. 3 according to the example of FIGS. 4 and 5, while e.g. the structured light camera 44 may be omitted therefrom.

Figure 8A:
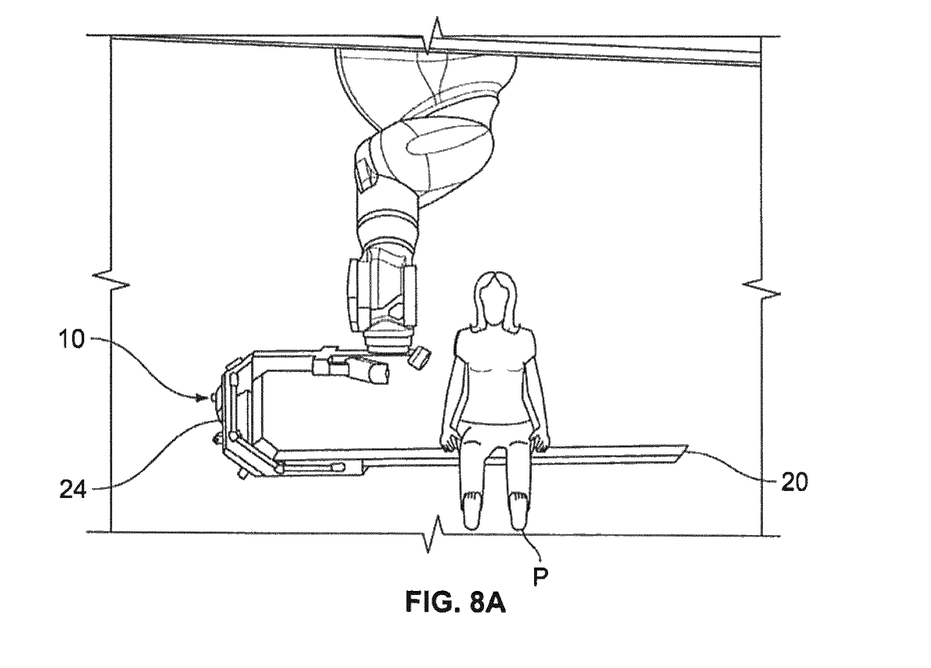
FIGS. 8a-8c show a sequence according to which a patient may assume a "head-first" treatment position within the patient support device.
Figure 8B:
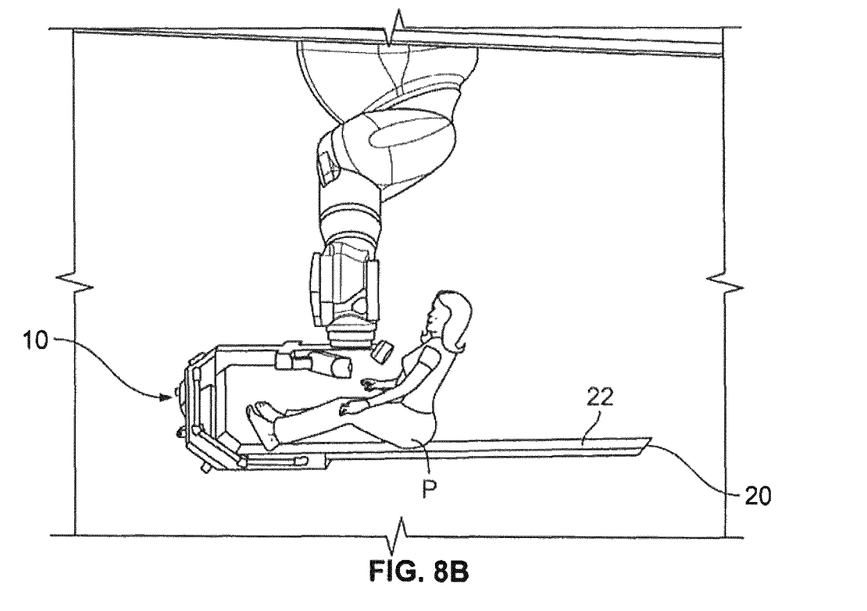
Figure 8C:
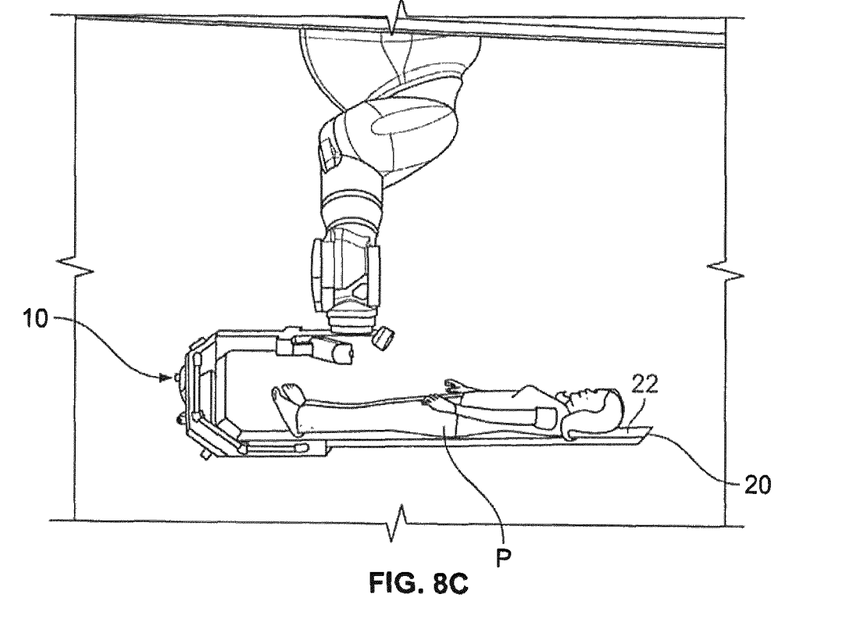

In the following, a sequence according to which a patient may assume a "head-first" treatment position within the patient support device 10 will be described with reference to FIGS. 8a-8c. The "head-first"-position generally relates a position according to which the patient P enters a work space of the medical imaging or radiotherapy device with the head first. According to FIG. 8a, the patient P first sits on the couchtop 20 to then swing his legs around towards the connecting region 24 (cf. FIG. 8b). Following that, the patient P lies down with the back resting against the front area 22 of the couchtop 20 (i.e., the patient P facing the ceiling area of the treatment room). This way, the patient P assumes a substantially horizontal treatment position in which he/she is stably and comfortably supported by the patient support device 10.

With reference to FIGS. 9a-9d, a sequence according to which a patient may assume a "feet-first" treatment position within the patient support device 10 will now be described. Similar to above, the "feet-first"-position generally relates a position according to which the patient P enters a work space of the medical imaging or radiotherapy device with the feet first. Note that in the shown example, the patient support region 18 and, more specifically, the couchtop 20 comprises a movable member 64 which is displaceable relative to the remaining and as such stationary parts of the patient support device 10, such as the connecting region 24 or coupling region 26. Note that the term stationary in this context relates to not moving relative to a geometric centre or centre of gravity of the patient support device 10 and does not consider movements of the patient support device 10 as a whole as carried out by the robot 16.

The movable member 64 is configured as a plate member defining a portion of the laying area of the couchtop 20. In general, said member 64 is connected to edge regions 66 of the couchtop 20 by way of guide structures 68 comprising rollers (which are held in the box-shaped member at the edge regions 66 of FIG. 9a). The guide structures 68 further comprise linear guide rails at said edge regions 66 in which these rollers are received. Accordingly, the movable member 64 can be displaced along a length of the patient support region 18 within the support plane S, i.e. pushed towards and pulled away from the connecting region 24.

Figure 9A:
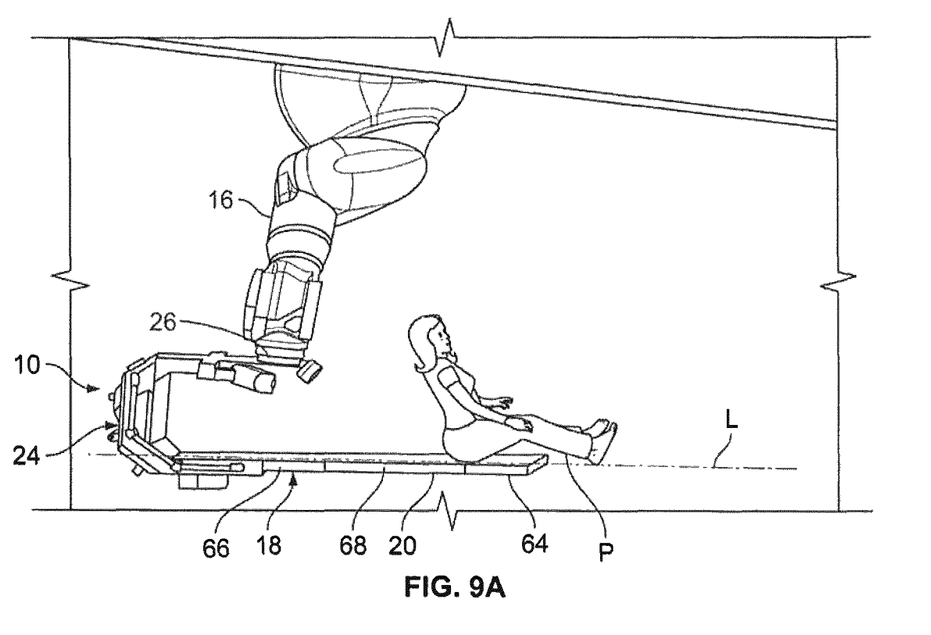
FIGS. 9a-9d show a sequence according to which a patient may assume a "feet-first" treatment position within the patient support device, including displacing a displaceable member of the patient support device.

In the state of FIG. 9A, the movable member 64 is displaced by a maximum degree, i.e. pulled away from the connecting region 24 by the largest possible amount, so that the patient support region 18 assumes a maximum length (cf. longitudinal or length-axis L as indicated in FIG. 9a). Accordingly, the patient P can sit on the movable member 64 with the legs oriented along a length of the patient support region 18 and couchtop 20 (note: this is different from the seating position in FIG. 8a in which the legs are oriented transversely to said length).

Figure 9B:
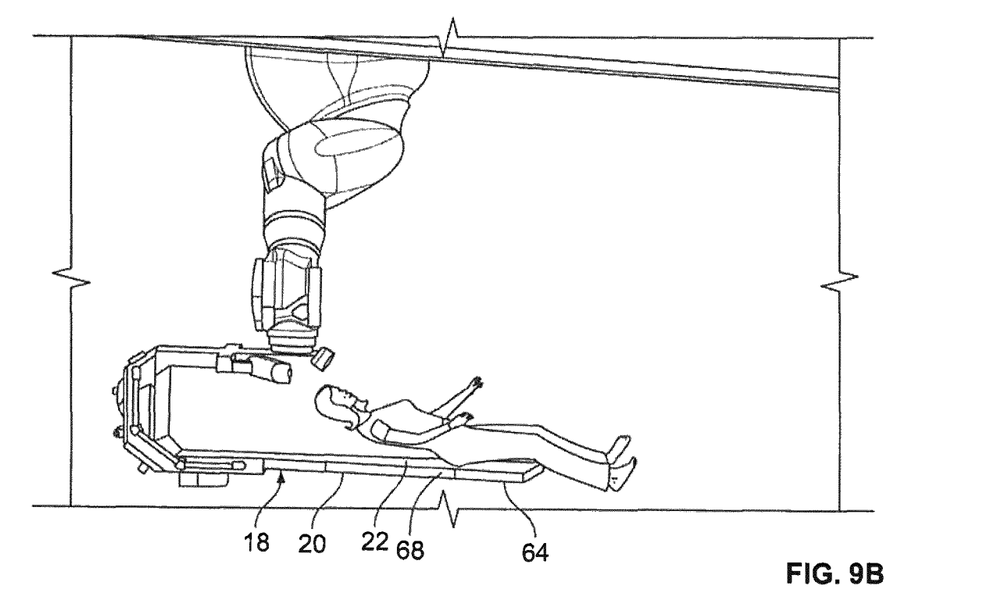
Figure 9C:
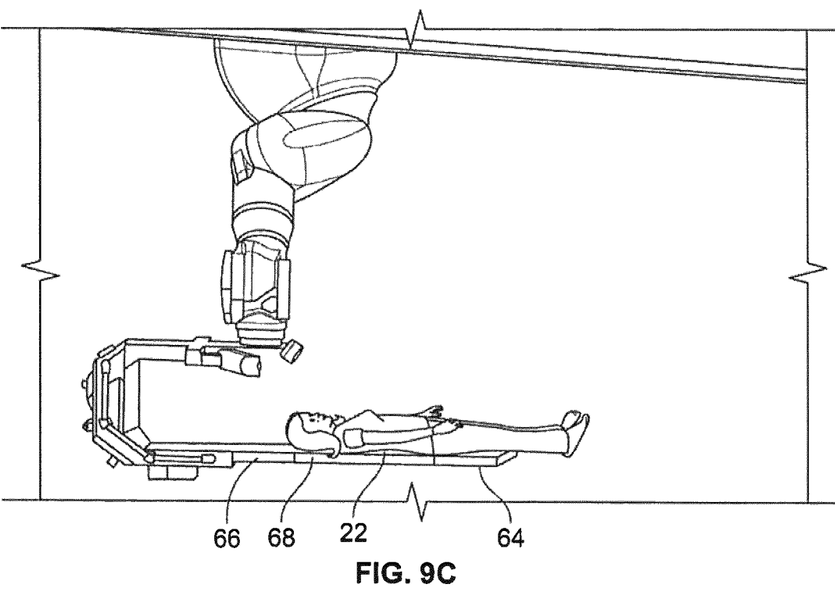
Figure 9D:
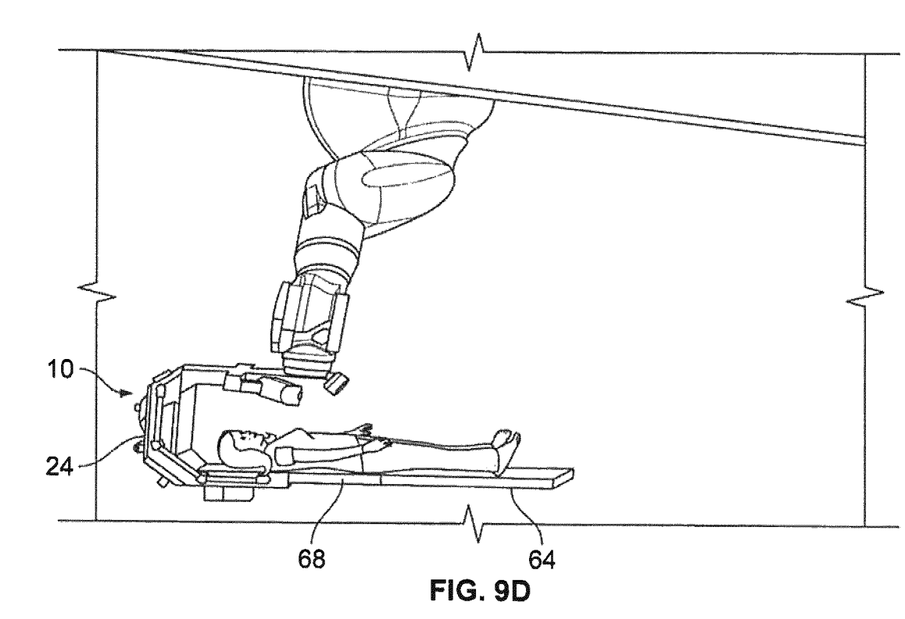

Following that, the patient bends backwards as indicated in FIGS. 9b and 9c until the back rests against a front area 22 of the patient support region 18 as defined by the movable member 64. Following that, the movable member 64 is be pushed towards the connecting region 24. For doing so, the box-shaped member of the guide structures 68 holding the rollers slides along the guide rails at the edge regions 66. This is evident from comparing the position of said box-shaped member in FIGS. 9c and 9d. In summary, the movable member 64 is thus slidingly displaced by pushing it onto and along the patient support region 18 and the remaining parts of the couchtop 20 towards the connecting region 24 in a trolley-like manner, thereby reducing a length of said patient support region 18. When this is completed, the patient assumes a predetermined treatment position as shown in FIG. 9d in which the patient positioning system 10 is further substantially self-balancing. Note that the concept of a movable member 64 may be integrated into any of the previously discussed examples according to FIGS. 1-8 or in any combinations thereof.

Figure 10:
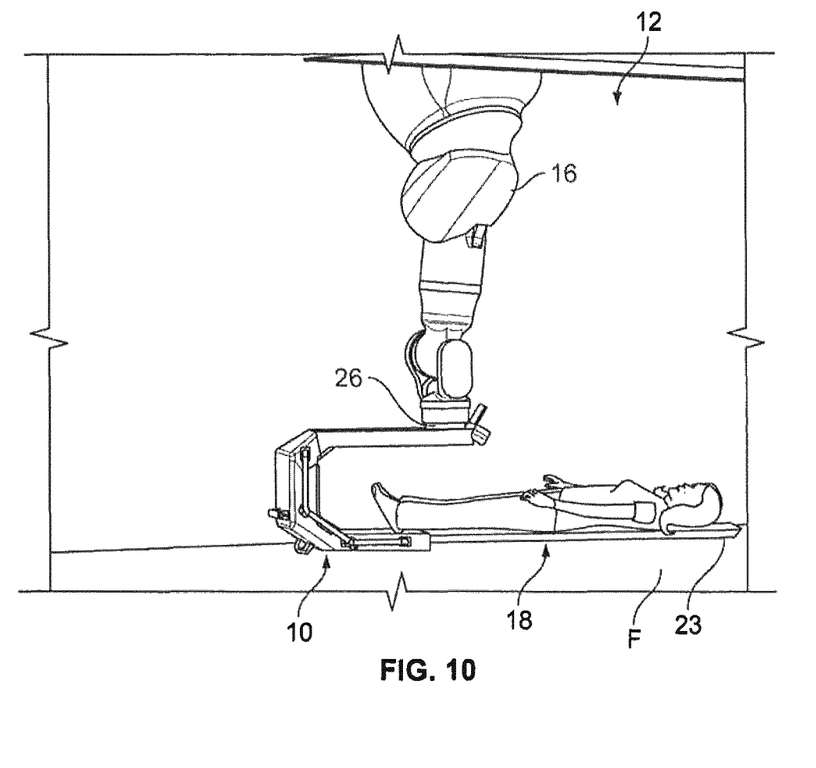
FIG. 10 shows a state in which the positioning system according to the first embodiment arranges the patient support device near a floor area of a treatment room.

FIG. 10 shows a state in which the positioning system 12 according to the first embodiment arranges the patient support device 10 near a floor area F of a treatment room. One can see that the patient support device 10 can in fact be positioned on or at least very close to the floor area F. In this case, the rotational joint R1-R5 of the robot 16 are oriented such that the robot 16 assumes a substantially vertically upright position (with a downwards orientation of the wrist section). This state is further marked by an increased length of the robot 16 (i.e., the links of the robot 16 are oriented so as to define an increased length of its kinematic chain). Note that this placement near or on the floor area F is possible in particular due to providing the coupling region 26 of the patient support device 10 on an upper side area and above the patient support region 18 and support plane S (cf. previous discussion). By doing so, the number and dimensions of interfering structures at the underside area 23 of the patient support region 18 can be significantly reduced or even completely omitted.

Figure 11A:
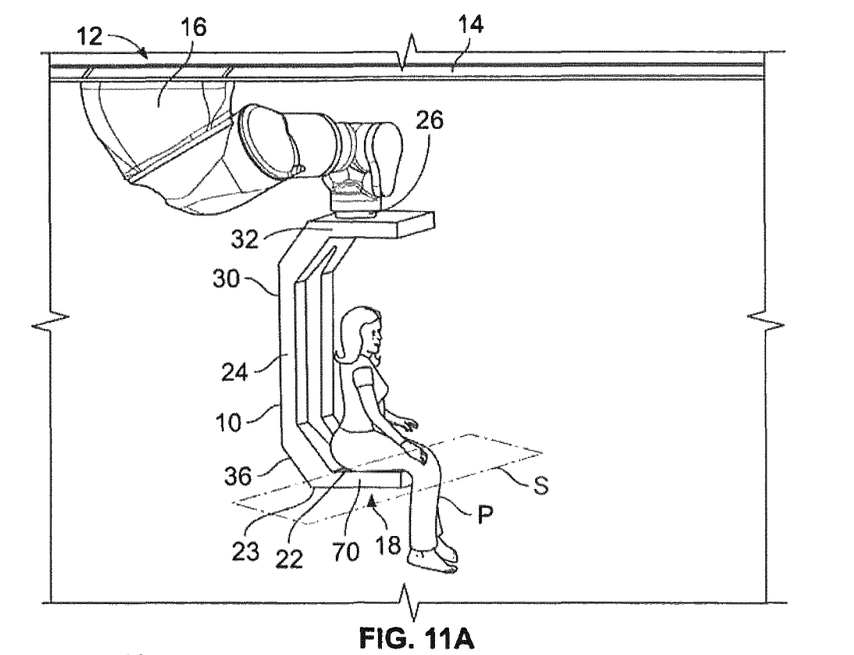
FIGS. 11a-11b shows a patient support device according to a further embodiment, wherein the patient support device comprises a patient seat.
Figure 11B:
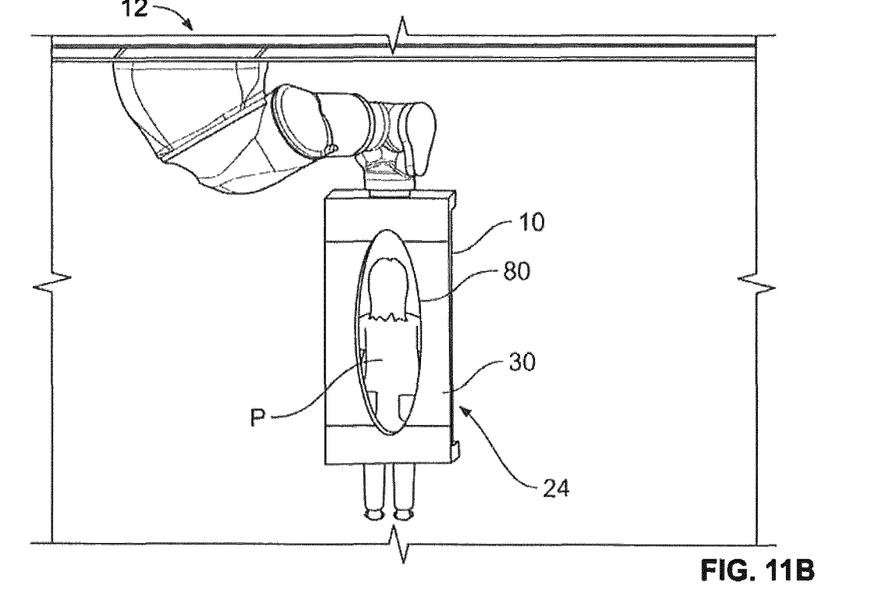

In FIGS. 11a-11b a positioning system 12 similar to the previous examples is shown (i.e. comprising a similar robot 16 and linear axis 14) which is connected to a patient support device 10 according to a further embodiment. More precisely the patient support region 18 of the patient support device 10 comprises a patient seat 70, said seat 70 defining a seating area at the front area 22 of the patient support region 18. Accordingly, as shown in FIG. 11a, a patient can sit on the seat 70 in a substantially upright manner. Again, it is evident that the front area 22 of the patient support region 18 thus defines a (virtual) support plane S which extends between a coupling region 26 to the robot 16 and an underside area 23 of the patient support region 18. Similar to above, the robot 16 can thus connect to the patient support device 10 at an upper side area and hence from above, instead of connecting to the underside area 23. Thus, the patient support device 10 is again arranged at the ceiling mounted robot 16 in a substantially hanging-configuration.

Note that the basic structure of the patient support device 10 is again similar to the previous examples by further comprising a connecting region 24 having an upright central section 30 extending orthogonally to the support plane S. Furthermore, a top section 32 is shown which connects to the coupling region 26 and merges into the central section 32 by way of an angled portion 34. Similarly, a lower portion 36 is provided which is extends in an angled manner from the central section 32 to merge into the patient seat 70. Thus, the patient positioning device 10 and in particular its connecting region 24 again defines an overall C- or bow-shape.

In FIG. 11b, a view of the rear side of the central section 30 of the connecting region 24 is shown. One can see, that said central section 30 is provided with a radiation-permeable area configured as a through-hole 80. This way, a back or neck area of the patient P can be radiated without interfering with the material of the patient positioning device 10.

The invention claimed is:

1. Patient support device that is connectable to a positioning system, the patient support device comprising:
   a patient support region, comprising a front area which defines a support plane for supporting and/or contacting a patient and an underside area substantially facing away from the front area; and
   a coupling region that is configured to be coupled to the positioning system, wherein the support plane at least partially extends between the coupling region and the underside area, wherein the coupling region and patient support region are connected by a connecting region which at least partially extends at an angle to the support plane, wherein the connecting region comprises a top section, a central section, and a lower section, wherein the lower section extends along and partially overlaps the underside area of the patient support region at an end of the patient support region, an wherein the coupling region is arranged in such a manner that it is configured to be projected into the front area of the patient support region, and wherein said projection takes place along an axis extending substantially orthogonally to the support plane, wherein the axis of projection intersects a center of gravity of the patient support device in an unloaded state.

2. Patient support device according to claim 1, wherein the patient support region comprises at least one of a seating area and a laying area.

3. Patient support device according to claim 1, when the patient support region comprises at least one of a patient seat and a patient couchtop.

4. Patient support device according to claim 1, wherein the connecting region comprises at least one area which is permeable for at least one of medical radiotherapy radiation and medical imaging radiation, said area comprising a through-hole.

5. Patient support device according to claim 1, wherein the patient support device comprises at least one movement instruction device for receiving operator inputs for moving the patient support device by way of the positioning system.

6. Patient support device according to claim 1, wherein the patient support device comprises at least one patient monitoring system, and wherein said patient monitoring system is configured to acquire information for monitoring at least one of a position of the patient and movements of the patient.

7. Patient support device according to claim 1, wherein the patient support device comprises at least one display device that is configured to display information to at least one of an operator of the patient support device and the patient being accommodated in the patient support device.

8. Patient support device according to claim 1, wherein the patient support device comprises at least one detection system for detecting at least one of a predetermined target in the surrounding and a deformation state of the patient support region under a patient's load, and wherein the detection system comprises an optical detection system which is arranged at or adjacent to the underside area of the patient support region.

9. Patient support device according to claim 1, wherein the patient support device further comprises at least one internal channel for accommodating connecting lines, and wherein said internal channel is configured to at least partially shield the connecting lines from the environment.

10. Patient positioning arrangement, comprising a patient support device according to claim 1 and a patient positioning system connected to the patient support device, and wherein the patient positioning system is ceiling mounted and/or comprises at least one of a multi-joint robot and a linear axis.

11. Patient support device according to claim 1, wherein a movable member is longitudinally displaceable relative to a remainder of the patient support region for adjusting a length of the patient support region.

12. Patient support device according to claim 1, wherein a movable member is displaceable within the support plane relative to the connecting region.

13. Patient support device according to claim 1, wherein the patient support region further comprises: edge regions extending from the connecting region; and guide structures connecting a movable member to the edge regions such that the movable member is displaceable relative to the edge regions and within the support plane.

14. Patient support device according to claim 1, wherein the coupling region is configured to be projected into the front area of the patient support region on a top side thereof.

15. Patient support device according to claim 1, wherein the patient support region comprises a movable member defining at least part of the front area, the movable member being configured to be moved in such a manner that a patient's position within the patient support device can be changed.

16. Patient support device according to claim 1, wherein the end of the patient support region, which the lower section extends along and partially overlaps, is a first end of the patient support region, wherein the patient support region further comprises a second end opposite to the first end, and wherein the second end is unsupported.

17. Patient support device according to claim 1, wherein the end of the patient support region, to which the coupling region is coupled to, is a first end of the patient support region, wherein the patient support region further comprises a second end opposite to the first end, and wherein the second end is unsupported.

18. Patient support device according to claim 1, further comprising a first angled portion extending from the lower section to the central section and a second angled portion extending from the top section to the central section, the first and second angled portions extending transverse to the central section.

19. Patient support device that is connectable to a positioning system, the patient support device comprising: a patient support region, comprising a front area which defines a support plane for supporting and/or contacting a patient and an underside area substantially facing away from the front area; and a coupling region that is configured to be coupled to the positioning system, wherein the support plane at least partially extends between the coupling region and the underside area, wherein the coupling region and patient support region are connected by a connecting region which at least partially extends at an angle to the support plane, wherein the connecting region comprises a top section, a central section and a lower section, wherein the lower section extends along and partially overlaps the underside area of the patient support region at an end of the patient support region, wherein the connecting region is at least one of substantially bow-, arc-, or c-shaped, and wherein the coupling region is arranged in such a manner that it is configured to be projected into the front area of the patient support region, and wherein said projection takes place along an axis extending substantially orthogonally to the support plane, wherein the axis of projection intersects a center of gravity of the patient support device, and wherein the axis of projection intersects a center of gravity of the patient support device in an unloaded state.

20. Patient support device according to claim 15, wherein the movable member is configured to at least partially support a patient and, wherein the movable member comprises at least part of a seating and/or laying area of the patient support region.

* * * * *